United States Patent [19]

Kingsman et al.

[11] Patent Number: 4,918,166
[45] Date of Patent: Apr. 17, 1990

[54] PARTICULATE HYBRID HIV ANTIGENS

[75] Inventors: Alan J. Kingsman; Susan M. Kingsman, both of Islip; Sally E. Adams, Kidlington, all of United Kingdom

[73] Assignee: Oxford Gene Systems Limited, Oxford, England

[21] Appl. No.: 112,083

[22] Filed: Oct. 26, 1987

Related U.S. Application Data

[63] Continuation of Ser. No. 36,888, Apr. 10, 1987.

[51] Int. Cl.⁴ .................... C07K 15/04; C07K 15/14; C07K 17/00; G01N 33/569
[52] U.S. Cl. .................................. 530/350; 424/89; 530/395; 530/403; 530/806; 530/812; 530/824; 530/826; 435/5
[58] Field of Search ...................... 435/5, 172.3, 320; 530/350, 387, 395, 412, 403, 806, 812, 824, 826; 424/89

[56] References Cited

U.S. PATENT DOCUMENTS 4,722,840  2/1988  Valenzuela et al. .................. 424/88

FOREIGN PATENT DOCUMENTS

86/07090  12/1986  World Int. Prop. O. ....... 435/172.3

OTHER PUBLICATIONS

Wilson et al., "Expression Strategies of the Yeast Retrotransposon Ty: A Short Sequence Directs Ribosomal Frameshifting", Nucl. Acids Res., 14 (1986), 7001–7016.
Putney et al., "HTLV-III/LAV-Neutralizing Antibodies to an *E. Coli*-Produced Fragment of the Virus Envelope", Science, 234 (1986), 1392–1395.
Lasky et al., "Neutralization of the Aids Retrovirus by Antibodies to a Recombinant Envelope Glycoprotein", Science, 233 (1986), 209–212.
Dobson et al., "The Identification and High Level Expression of a Protein Encoded by the Yeast Ty Element", Embo J., 3 (1984), 1115–1119.
Malim et al., "The Production of Hybrid Ty:IFN Virus-Like Particles in Yeast", Nucl. Acids Res., 15 (1987), 7571–7580.
Fulton et al., "Variants Within the Yeast Ty Sequence Family Encode a Class of Structurally Conserved Proteins", Nucl. Acids Res., 13 (1985), 4097–4112.
Mellor et al., "Reverse Transcriptase Activity and Ty RNA are Associated with Virus-Like Particles in Yeast", Nature, 318 (1985), 583–586.
Mellor et al., "A Retrovirus-Like Strategy for Expression of a Fusion Protein Encoded by Yeast Transposon Ty 1", Nature, 313 (1985), 243–246.

Primary Examiner—Christine M. Nucker
Attorney, Agent, or Firm—Allegretti & Witcoff, Ltd.

[57] ABSTRACT

Fusion proteins comprise a77 first amino acid sequence and a second amino acid sequence. The first amino acid sequence is derived from a retrotransposon or an RNA retrovirus and confers on the fusion protein the ability to assemble into particles; an example is the product of the TYA gene of the yeast retrotransposon Ty. The second amino acid sequence is an HIV antigen. So particles formed of the fusion proteins may be useful in vaccines or in diagnostic or purification applications.

3 Claims, 13 Drawing Sheets

FIG. 4 pMA5620  AAA GCC GGA TCC GGG AAA TAA
                     BamHI pMA5621  AAA GCC GGA TCA AGG ATC CGA TCC GGG AAA
         TTA                 BamHI pMA5622  AAA GCC GGA TCG GAT CCG ATC CGG GAA ATA A
                     BamHI

FIG. 6

| | |
|---|---|
| hiv3 | GTA CCT GTG |
| hiv4 | A AAA CAG |
| hiv5 | A AAG TGC |
| hiv6 | G ATC TGT AGT |
| hiv7 | GAT CAA AGC CTA |
| hiv8 | GA TCT GTC AAT |
| hiv9 | G ATC TTC AGA CCT |
| hiv10 | GAT CAA CAG CTC |

T5620-hiv 5

Nucleotide sequence and deduced amino acid sequence at the TYA-hiv22 junction in the plasmid pMA5620-hiv22:

```
aaa  gcc  gga  tcA  GCT  TTA  GAC  AAG
 K    A    G    S    A    L    D    L
```

FIG. 10

```
ATGGAATCCCAACAATTATCTCAACATTCACCCATTTCTCATGGTAGC
 M  E  S  Q  Q  L  S  Q  H  S  P  I  S  H  G  S

GCCTGTGCTTCGGTTACTTCTAAGGAAGTCCACACAAATCAAGATCCG
 A  C  A  S  V  T  S  K  E  V  H  T  N  Q  D  P

TTAGACGTTTCAGCTTCCAAAACAGAAGAATGTGAGAAGGCTTCCACT
 L  D  V  S  A  S  K  T  E  E  C  E  K  A  S  T

AAGGCTAACTCTCAACAGACAACAACACCTGCTTCATCAGCTGTTCCA
 K  A  N  S  Q  Q  T  T  T  P  A  S  S  A  V  P

GAGAACCCCCATCATGCCTCTCCTCAAACTGCTCAGTCACATTCACCA
 E  N  P  H  H  A  S  P  Q  T  A  Q  S  H  S  P

CAGAATGGGCCGTACCCACAGCAGTGCATGATGACCCAAAACCAAGCC
 Q  N  G  P  Y  P  Q  Q  C  M  M  T  Q  N  Q  A

AATCCATCTGGTTGGTCATTTTACGGACACCCATCTATGATTCCGTAT
 N  P  S  G  W  S  F  Y  G  H  P  S  M  I  P  Y

ACACCTTATCAAATGTCGCCTATGTACTTTCCACCTGGGCCACAATCA
 T  P  Y  Q  M  S  P  M  Y  F  P  P  G  P  Q  S

CAGTTTCCGCAGTATCCATCATCAGTTGGAACGCCTCTGAGGACTCCA
 Q  F  P  Q  Y  P  S  S  V  G  T  P  L  R  T  P

TCACCTGAGTCAGGTAATACATTTACTGATTCATCCTCACGCGACTCT
 S  P  E  S  G  N  T  F  T  D  S  S  A  D  S

GATATGACATCCACTAAAAAATATGTCAGACCACCACCAATGTTAACC
 D  M  T  S  T  K  K  Y  V  R  P  P  P  M  L  T

TCACCTAATGACTTTCCAAATTGGGTTAAAACATACATCAAATTTTTA
 S  P  N  D  F  P  N  W  V  K  T  Y  I  K  F  L

CAAAACTCGAATCTCGGTGGTATTATTCCGACAGTAAACGGAAAACCC
 Q  N  S  N  L  G  G  I  I  P  T  V  N  G  K  P

GTACGTCAGATCACTGATGATGAACTCACCTTCTTGTATAACACTTTT
 V  P  Q  I  T  D  D  E  L  T  F  L  Y  N  T  F

CAAATATTTGCTCCCTCTCAATTCCTACCTACCTGGGTCAAAGACATC
 Q  I  F  A  P  S  Q  F  L  P  T  W  V  K  D  I

CTATTCGTTGATTATACGGATATCATGAAAATTCTTTCCAAAAGTATT
 L  S  V  D  Y  T  D  I  M  K  I  L  S  K  S  I
```

FIG.10 CONT.¹

```
GAAAAAATGCAATCTGATACCCAAGAGGCAAACGACATTGTGACCCTG
 E  K  M  Q  S  D  T  Q  E  A  N  D  I  V  T  L

GCAAATTTGCAATATAATGGCAGTACACCTGCAGATGCATTTGAAACA
 A  N  L  Q  Y  N  G  S  T  P  A  D  A  F  E  T

AAAGTCACAAACATTATCGACAGACTGAACAATAATGGCATTCATATC
 K  V  T  N  I  I  D  R  L  N  N  N  G  I  H  I

AATAACAAGGTCGCATGCCAATTAATTATGAGAGGTCTATCTGGCGAA
 N  N  K  V  A  C  Q  L  I  M  R  G  L  S  G  E

TATAAATTTTTACGCTACACACGTCATCGACATCTAAATATGACAGTC
 Y  K  F  L  R  Y  T  R  H  R  H  L  N  M  T  V

GCTGAACTGTTCTTAGATATCCATGCTATTTATGAAGAACAACAGGGA
 A  E  L  F  L  D  I  H  A  I  Y  E  E  Q  Q  G

TCGAGAAACAGTAAACCTAATTACAGGAGAAATCCGAGTGATGAGAAG
 S  R  N  S  K  P  N  Y  R  R  N  P  S  D  E  K

AATGATTCTCGCAGCTATACGAATACAACCAAACCCAAAGccggatcA
 N  D  S  R  S  Y  T  N  T  T  K  P  K  A  G  S GCTTTAGACAAGATAGAGGAAGAGCAAAACAAAAGTAAGAAAAAAGCA
 A  L  D  L  I  E  E  E  Q  N  K  S  K  K  K  A CAGCAAGCAGCAGCTGACACAGGACACAGCAGTCAGGTCAGCCAAAAT
 Q  Q  A  A  A  D  T  G  H  S  S  Q  V  S  Q  N TACCCTATAGTGCAGAACATCCAGGGGCAAATGGTACATCAGGCCATA
 Y  P  I  V  Q  N  I  Q  G  Q  M  V  H  Q  A  I TCACCTAGAACTTTAAATGCATGGGTAAAAGTAGTAGAAGAGAAGGCT
 S  P  R  T  L  N  A  W  V  K  V  V  E  E  K  A TTCAGCCCAGAAGTAATACCCATGTTTTCAGCATTATCAGAAGGAGCC
 F  S  P  E  V  I  P  M  F  S  A  L  S  E  G  A ACCCCACAAGATTTAAACACCATGCTAAACACAGTGGGGGGACATCAA
 T  P  Q  D  L  N  T  M  L  N  T  V  G  G  H  Q GCAGCCATGCAAATGTTAAAAGAGACCATCAATGAGGAAGCTGCAGAA
 A  A  M  Q  M  L  K  E  T  I  N  E  E  A  A  E TGGGATAGAGTACTACCAGTGCATGCAGGGCCTATTGCACCAGGCCAG
 W  D  R  V  H  P  V  H  A  G  P  I  A  P  G  Q
```

FIG. 10 CONT.²

```
ATG AGA GAA CCA AGG GGA AGT GAC ATA GCA GGA ACT ACT AGT ACC CTT
 M   R   E   P   R   G   S   D   I   A   G   T   T   S   T   L

CAG GAA CAA ATA GGA TGG ATG ACA AAT AAT CCA CCT ATC CCA GTA GGA
 Q   E   Q   I   G   W   M   T   N   N   P   P   I   P   V   G

GAA ATT TAT AAA AGA TGG ATA ATC CTG GGA TTA AAT AAA ATA GTA AGA
 E   I   Y   K   R   W   I   I   L   G   L   N   K   I   V   R

ATG TAT AGC CCT ACC AGC ATT CTG GAC ATA AGA CAA GGA CCA AAA GAA
 M   Y   S   P   T   S   I   L   D   I   R   Q   G   P   K   E

CCT TTT AGA GAC TAT GTA GAC CGG TTC TAT AAA ACT CTA AGA GCC GAG
 P   F   R   D   Y   V   D   R   F   Y   K   T   L   R   A   E

CAA GCT gatccggggaaataaattgaattga
 Q   A   D   P   G   N   K   L   N   *
```

FIG. 11a oligonucleotide hiv31

```
        10         20         30         40
5' GATCTGGTGT TGCTCCAACT AAGGCTAAGA GAAGAGTTGT
3'     ACCACA ACGAGGTTGA TTCCGATTCT CTTCTCAACA 50         60         70         80
   TCAAAGAGAA AAGAGAGCTG TTGGTATTGG TGCTTTGTTC
   AGTTTCTCTT TTCTCTCGAC AACCATAACC ACGAAACAAG 90        100
   TTGGGTTTCT TGGGTGCTGC TGGTG      3'
   AACCCAAAGA ACCCACGACG ACCACCTAG  5'
```

FIG. 11b oligonucleotide hiv32

```
        10         20         30         40
5' GATCTTTCTG TGCTTCTGAC GCTAAGGCTT ACGACACTGA
3'     AAAGAC ACGAAGACTG CGATTCCGAA TGCTGTGACT 50         60         70         80
   AGTTCACAAC GTTTGGGCTA CTCACGCTTG TGTTCCAACT
   TCAAGTGTTG CAAACCCGAT GAGTGCGAAC ACAAGGTTGA 90        100        110
   GACCCAAACC CACAAGAAGT TGTTTTGGTT AACG      3'
   CTGGGTTTGG GTGTTCTTCA ACAAAACCAA TTGCCTAG  5'
```

FIG. 12

```
ATG GAATCC CAACAATTA CTC AACAT TCA CCC ATT TCT CAT GGT AGC
 M   E  S   Q  Q  L   S  Q   H   S   P   I   S   H   G   S

GCC TGT GCT TCG GTT ACT TCT AAG GAA GTC CAC ACA AAT CAA GAT
 A   C   A   S   V   T   S   K   E   V   H   T   N   Q   D

CCG TTA GAC GTT TCA GCT TCC AAA ACA GAA GAA TGT GAG AAG GCT TCC
 P   L   D   V   S   A   S   K   T   E   E   C   E   K   A   S

ACT AAG GCT AAC TCT CAA CAG ACA ACA ACA CCT GCT TCA TCA GCT GTT
 T   K   A   N   S   Q   Q   T   T   T   P   A   S   S   A   V

CCA GAG AAC CCC CAT CAT GCC TCT CCT CAA ACT GCT CAG TCA CAT TCA
 P   E   N   P   H   H   A   S   P   Q   T   A   Q   S   H   S

CCA CAG AAT GGG CCG TAC CCA CAG CAG TGC ATG ATG ACC CAA AAC CAA
 P   Q   N   G   P   Y   P   Q   Q   C   M   M   T   Q   N   Q

GCC AAT CCA TCT GGT TGG TCA TTT TAC GGA CAC CCA TCT ATG ATT CCG
 A   N   P   S   G   W   S   F   Y   G   H   P   S   M   I   P

TAT ACA CCT TAT CAA ATG TCG CCT ATG TAC TTT CCA CCT GGG CCA CAA
 Y   T   P   Y   Q   M   S   P   M   Y   F   P   P   G   P   Q

TCA CAG TTT CCG CAG TAT CCA TCA TCA GTT GGA ACG CCT CTG AGG ACT
 S   Q   F   P   Q   Y   P   S   S   V   G   T   P   L   R   T

CCA TCA CCT GAG TCA GGT AAT ACA TTT ACT GAT TCA TCC TCA GCG GAC
 P   S   P   E   S   G   N   T   F   T   D   S   S   S   A   D

TCT GAT ATG ACA TCC ACT AAA AAA TAT GTC AGA CCA CCA CCA ATG TTA
 S   D   M   T   S   T   K   K   Y   V   R   P   P   P   M   L

ACC TCA CCT AAT GAC TTT CCA AAT TGG GTT AAA ACA TAC ATC AAA TTT
 T   S   P   N   D   F   P   N   W   V   K   T   Y   I   K   F

TTA CAA AAC TCG AAT CTC GGT GGT ATT ATT CCG ACA GTA AAC GGA AAA
 L   Q   N   S   N   L   G   G   I   I   P   T   V   N   G   K

CCC GTA CGT CAG ATC ACT GAT GAT GAA CTC ACC TTC TTG TAT AAC ACT
 P   V   P   Q   I   T   D   D   E   L   T   F   L   Y   N   T

TTT CAA ATA TTT GCT CCT CTC AAT TCC TAC CTA CCT GGG TCA AAG AC
 F   Q   I   F   A   P   S   Q   F   L   P   T   W   V   K   D

ATC CTA TCC GTT GAT TAT ACG GAT ATC ATG AAA ATT CTT TCC AAA AGT
 I   L   S   V   D   Y   T   D   I   M   K   I   L   S   K   S
```

FIG. 12 CONT.[1]

```
ATTGAAAAAATGCAATCTGATACCCAAGAGGCAAACGACATTGTGACC
 I  E  K  M  Q  S  D  T  Q  E  A  N  D  I  V  T

CTGGCAAATTTGCAATATATTGGCAGTACACCTGCAGATGCATTTGAA
 L  A  N  L  Q  Y  N  G  S  T  P  A  D  A  F  E

ACAAAAGTCACAAACATTATCGACAGACTGAACAATAATGGCATTCAT
 T  K  V  T  N  I  I  D  R  L  N  N  N  G  I  H

ATCAATAACAAGGTCGCATGCCAATTAATTATGAGAGGTCTATCTGGC
 I  N  N  K  V  A  C  Q  L  I  M  R  G  L  S  G

GAATATAAATTTTTACGCTACACACGTCATCGACATCTAAATATGACA
 E  Y  K  F  L  R  Y  T  R  H  R  H  L  N  M  T

GTCGCTGAACTGTTCTTAGATATCCATGCTATTTATGAAGAACAACAG
 V  A  E  L  F  L  D  I  H  A  I  Y  E  E  Q  Q

GGATCGAGAAACAGTAAACCTAATTACAGGAGAAATCCGAGTGATGAG
 G  S  R  N  S  K  P  N  Y  R  R  N  P  S  D  E

AAGAATGATTCTCGCAGCTATACGAATACAACCAAACCCAAAGccgGA
 K  N  D  S  R  S  Y  T  N  T  T  K  P  K  A  G TCTGGTGTTGCTCCAACTAAGGCTAAGAGAAGAGTTGTTCAAAGAGAA
 S  G  V  A  P  T  K  A  K  R  R  V  V  Q  R  E AAGAGAGCTGTTGGTATTGGTGCTTTGTTCTTGGGTTTCTTGGGTGCT
 K  R  A  V  G  I  G  A  L  F  L  G  F  L  G  A GCTGGTGgatccgggaaataa
 A  G  G  S  G  K  *
```

FIG. 13

```
ATGGAATCCCAACAATTATCTCAACATTCACCCATTTCTCATGGTAGC
 M  E  S  Q  Q  L  S  Q  H  S  P  I  S  H  G  S

GCCTGTGCTTCGGTTACTTCTAAGGAAGTCCACACAAATCAAGATCCG
 A  C  A  S  V  T  S  K  E  V  H  T  N  Q  D  P

TTAGACGTTTCAGCTTCCAAAACAGAAGAATGTGAGAAGGCTTCCACT
 L  D  V  S  A  S  K  T  E  E  C  E  K  A  S  T

AAGGCTAACTCTCAACAGACAACAACACCTGCTTCATCAGCTGTTCCA
 K  A  N  S  Q  Q  T  T  T  P  A  S  S  A  V  P

GAGAACCCCCATCATGCCTCTCCTCAAACTGCTCAGTCACATTCACCA
 E  N  P  H  H  A  S  P  Q  T  A  Q  S  H  S  P

CAGAATGGGCCGTACCCACAGCAGTGCATGATGACCCAAAACCAAGCC
 Q  N  G  P  Y  P  Q  Q  C  M  M  T  Q  N  Q  A

AATCCATCTGGTTGGTCATTTTACGGACACCCATCTATGATTCCGTAT
 N  P  S  G  W  S  F  Y  G  H  P  S  M  I  P  Y

ACACCTTATCAAATGTCGCCTATGTACTTTCCACCTGGGCCACAATCA
 T  P  Y  Q  M  S  P  M  Y  F  P  P  G  P  Q  S

CAGTTTCCGCAGTATCCATCATCAGTTGGAACGCCTCTGAGGACTCCA
 Q  F  P  Q  Y  P  S  S  V  G  T  P  L  R  T  P

TCACCTGAGTCAGGTAATACATTTACTGATTCATCCTCAGCGGACTCT
 S  P  E  S  G  N  T  F  T  D  S  S  S  A  D  S

GATATGACATCCACTAAAAAATATGTCAGACCACCACCAATGTTAACC
 D  M  T  S  T  K  K  Y  V  R  P  P  P  M  L  T

TCACCTAATGACTTTCCAAATTGGGTTAAAACATACATCAAATTTTTA
 S  P  N  D  F  P  N  W  V  K  T  Y  I  K  F  L

CAAAACTCGAATCTCGGTGGTATTATTCCGACAGTAAACGGAAAACCC
 Q  N  S  N  L  G  G  I  I  P  T  V  N  G  K  P

GTACGTCAGATCACTGATGATGAACTCACCTTCTTGTATAACACTTTT
 V  P  Q  I  T  D  D  E  L  T  F  L  Y  N  T  F

CAAATATTTGCTCCCTCTCAATTCCTACCTACCTGGGTCAAAGACATC
 Q  I  F  A  P  S  Q  F  L  P  T  W  V  K  D  I

CTATCCGTTGATTATACGGATATCATGAAAATTCTTTCCAAAAGTATT
 L  S  V  D  Y  T  D  I  M  K  I  L  S  K  S  I
```

FIG. 13CONT.¹

```
GAAAAAATG CAATCTGAT ACCCAAGAG GCAAAC GACATTGTGACCCTG
 E  K  M  Q  S  D  T  Q  E  A  N  D  I  V  T  L

GCAAATTTG CAATATAAT GGCAGTACACC TGCAGATGCA TTTGAAACA
 A  N  L  Q  Y  N  G  S  T  P  A  D  A  F  E  T

AAAGTCACAAACA TTATCGAC AGACTGAAC AATAATGGC ATTCATATC
 K  V  T  N  I  I  D  R  L  N  N  N  G  I  H  I

AATAACAAG GTCGCATGCCAA TTAAT TATGAGAGGTCTA TCTGGCGAA
 N  N  K  V  A  C  Q  L  I  M  R  G  L  S  G  E

TATAAATTT TTACGC TACACACGT CATCGACATC TAAATATGACAGTC
 Y  K  F  L  R  Y  T  R  H  R  H  L  N  M  T  V

GCT GAACTG TTCTTAGATATCCAT GCTATT TATGAAGAACAACAGGGA
 A  E  L  F  L  D  I  H  A  I  Y  E  E  Q  Q  G

TCGAGAAACAG TAAACCTAATTAC AGGAGAAATCCGAGTGATGAGAAG
 S  R  N  S  K  P  N  Y  R  R  N  P  S  D  E  K

AATGATTCTCGCAGC TATACGAAT ACAACC AAACCC AAAGccgGATCT
 N  D  S  R  S  Y  T  N  T  T  K  P  K  A  G  S TTCTGTGCTTCTGACGCTAAGG CTTACGACACTGAAGTTCACAACGTT
 F  C  A  S  D  A  K  A  Y  D  T  E  V  H  N  V TGGGCTACTCACGCTTGTGTTCCAACTGACCCAAACCCACAAGAAGTT
 W  A  T  H  A  C  V  P  T  D  P  N  P  Q  E  V GTTTTGGTTAACGgatccgggaaataa
 V  L  V  N  G  S  G  K  *
```

PARTICULATE HYBRID HIV ANTIGENS

This is a continuation-in-part of Ser. No. 07/036,888 filed Apr. 10, 1987.

FIELD OF INVENTION

The present invention relates to particulate Human Immunodeficiency Virus (HIV) antigens. In particular it relates to hybrid particles composed of fusion proteins comprising amino acid sequences encoded by the TYA gene of the yeast retrotransposon Ty and amino acid sequences encoded by HIV, vectors containing the genes for the fusion proteins, vectors for the high level expression of the hybrid particles and a method for the production of these particles in yeast. The Ty:HIV hybrid particles may be used as an HIV vaccine or as components of HIV diagnostic tests.

BACKGROUND ART

HIV, also known as LAV or HTLV III, is the causative agent of Acquired Immuno-Deficiency Syndrome (AIDS) (Barre-Sinoussi et al. 1983 Science 220, 868; Gallo et al. 1984 Science 224, 500; Levy et al. 1984 Science 225, 840; Clavel et al. 1986 Nature 324 691). At present there is no cure for AIDS nor is there a vaccine available. The genetic organization and the entire nucleotide sequence of HIV is know (Ratner et al. 1985 Nature 313, 277; Wain-Hobson et al. 1985 Cell 40, 9; Muesing et al. 1985 Nature 313 450; Sandoz-Pescador et al. 1985 Science 227 484). HIV is a lentivirus-like retrovirus with gag, pol and env genes like other retroviruses but it also contains additional coding sequences, sor, tat. art/trs and 3' orf that are involved in various aspects of virus replication and expression (Sodroski et al. 1985 Science 227, 171; Sodroski et al. 1986 Nature 319, 555; Sodroski et al. 1986 Nature 321, 412; Feinberg et al. 1986 Cell 46, 807) although the functions of sor and 3'orf are unclear.

Three general approaches can be used to produce an HIV vaccine. First, large amounts of HIV can be grown and inactivated to provide antigen. Second, recombinant DNA techniques can be used to produce HIV antigens either as simple monomeric proteins (e.g. Putney et al. (1986) Science 234 1392; Laskey et al. 1986 Science 233 209) or as vaccinia virus hybrids, although it is not clear that general use of a live vaccinia based system will ever be considered safe (e.g. Chakrabarti et al. 1986 Nature 320, 535; Zagury et al. 1987 Nature 326, 249). Third, synthetic peptides might be useful (Kennedy et al. 1986 Science 231 1556; Chanh et al. EMBO J. 5 3065).

Most of the work to date on producing HIV antigens has focussed on the production of the two surface glycoproteins encoded by the env gene, gp120 and gp41 (Putney et al. op. cit.; Laskey et al. op. cit.; Certa et al. 1986 EMBO J. 5 3051) although there has been some work on other antigens, e.g. tat III (Aldovini et al. 1986 PNAS 83 6672), sor (Kan et al. 1986 Science 231 1553), pol (Veronese et al. 1986 Science 233 1289; Kramer et al. 1986 Science 231 1580). The production of HIV antigens for vaccines or diagnostics and research material by recombinant DNA technology has three key advantages over production based on propagation of the virus. First, it is safe. Second, high yields can be achieved (Putney et al. op. cit.) by using high efficiency expression systems. Third, it is versatile in that antigenic domains that might normally be concealed may be exposed, a vaccine antigen could be marked with some other antigen to distinguish vaccination from infection or composite antigens might be produced.

A substantial disadvantage of most antigens produced by recombinant DNA techniques for vaccines is that they are usually made as simple monomeric proteins. This is not the ideal configuration for an immunising antigen as it does not readily permit the cross-linking of the components of the immune system that is required for maximum stimulation of humoral and cellular immunity. An ideal immunogen is a polymer of multiple antigenic determinants assembled into a high molecular weight carrier. A good immunogen should also have the maximum number epitopes exposed. This is best achieved by presenting multiple copies of the antigen on the surface of a particle. For this reason it would be desirable to develop polyvalent, particulate carrier systems for immunising antigens.

DISCLOSURE OF THE INVENTION

An entirely novel polyvalent antigen carrier particle, based on the ability of the p1 protein encoded by the TYA gene of the yeast retrotransposon Ty to form 60 nm particles known as Ty-VLPs (virus like particles), is the subject of U.K. Patent Application No. 8626148 [having a common assignee with this application.] p1 fusion proteins can be produced by construction of appropriate TYA hybrid genes comprising some of the coding region of TYA and the coding region of any antigen. These fusion proteins form hybrid Ty-VLPs and present the added antigen in a high molecular weight polyvalent particulate form that is ideal for the stimulation of the mammalian immune response. In the present invention this technology is applied to the production of particulate HIV antigens.

According to a first aspect, the present invention provides a fusion protein capable of assembling into a particle, the fusion protein comprising a first amino acid sequence and a second amino acid sequence, wherein the first amino acid sequence is substantially homologous with a particle-forming protein encoded by a retrotransposon or an RNA retrovirus and wherein the second amino acid sequence is substantially homologous with an HIV antigen, and wherein the second amino acid sequence does not form an amino acid sequence naturally directly fused to the first amino acid sequence by the said retrotransposon or RNA retrovirus.

According to a second aspect, the invention provides a particle comprising a plurality of fusion proteins, each fusion protein comprising a first amino acid sequence and a second amino acid sequence, wherein the first amino acid sequence is substantially homologous with a particle-forming protein encoded by a retrotransposon or an RNA retrovirus and wherein the second amino acid sequence is substantially homologous to an HIV antigen and not naturally fused to the first amino acid sequence by the said retrotransposon or RNA retrovirus.

These particles may be referred to as particulate HIV antigens.

Such particles will generally be substantially pure, by which is meant at least 5%, 10%, 20%, 50%, 80%, 90%, 95% or 99% by weight pure, in increasing order of preference.

A given particle may be composed of a plurality of different fusion proteins; that is to say fusion proteins having different second amino acid sequences from each other, thereby presenting different HIV antigens. Two, three or even more different second amino acid sequences may be present in a particle.

The first amino acid sequence may be the product of the yeast Ty TYA gene, the product of copia and copia-like elements from insects or the gag gene of a RNA retroviruses.

Retroviruses includes Human Immunodeficiency Virus I and II (HIV-I, HIV-II), Human T-cell Lymphotrophic Virus I and II (HTLV-I, HTLV-II), Murine Leukaemia Virus, Moloney Murine Leukaemia Virus, Mouse Mammary Tumour Virus, Avian Leukosis Virus. SIV, Feline Leukaemia Virus, Human B-cell Lymphotrophic Virus, and Bovine Leukaemia Virus. Retrotransposons indicated above, include the Ty element of yeast, the copia and copia-like elements of insects such as *Drosophilia melanozasterm,* VL30 in mice and IAP genes in mice.

Preferred retrotransposons include the yeast retrotransposon Ty. It has previously been shown that Ty directs the synthesis of 60 nm virus-like particles (Ty-VLPs) (Mellor et. al. 1985a Nature 318,513). It has now been discovered, among other things, that the p1 protein, encoded by the TYA gene does not appear to require further processing to produce Ty-VLPs. Therefore the Ty-encoded amino acid sequence is preferably the p1 protein encoded by the TYA gene. It is known (Fulton et al. NAR 13(11) 1985 4097) that both classes (I and II) of Ty make p1; so either class may be used.

The Ty-encoded amino acid sequence need not be the whole of the p1 protein; instead it may be a part of the p1 protein encoded by a part of the TYA gene, which part is capable of directing the synthesis of Ty virus-like particles (Ty-VLPs). Preferably the Ty-encoded amino acid sequence is derivable from the class I Ty element known as Ty1-15. The stop codon at the end of the TYA gene is preferably not included; if it is included, however, fusion protein may continue to be expressed, albeit at low yield, as it appears that the stop codon may be ignored with a frequency of about 1 in 20 times by the frameshifting mechanism described by Wilson et al. (NAR 14(17) 1986 7001).

The present invention is thus at least in part based on the discovery that Ty protein p1, the product of the TYA gene (Dobson et al. 1984 EMBO J 3, 1115) is sufficient to produce Ty-VLPs and that p1, among other things, is capable of being used in the formation of particles composed of fusion proteins.

The second amino acid sequence may be substantially homologous with (which term clearly includes "identical to") any HIV antigen. The HIV antigen may be an HIV-I or HIV-II antigen. It may be glycosylated or otherwise modified, whether by a natural post-transcriptional modification mechanism or otherwise (e.g. by chemical synthesis). In particular, the second amino acid sequence may be an HIV surface glycoprotein. Such glycoproteins (or at least some of them) are believed to be encoded by the env gene. Instances of these glycoproteins include gp120 and gp41.

Thus this invention includes as the second protein HIV antigens having substantially the same antigenicity as HIV antigen p24, p41, or p120.

A first part of the second amino acid sequence may be a linker sequence, which may in some circumstances be readily cleavable. The remainder of the second amino acid sequence may thus be cleaved off in a purifications step.

Particulate antigens in accordance with the invention may therefore be useful in the preparation of vaccines, which form a further aspect of the invention. The vaccine may comprise a particulate antigen and a physiologically acceptable non-toxic carrier, such as sterile physiological saline or sterile PBS. Sterility will generally be essential for parenterally administrable vaccines. One or more appropriate adjuvants may also be present. Examples of suitable adjuvants include muramyl dipeptide, aluminum hydroxide and saponin.

It should be noted that vaccines in accordance with the invention may present more than one antigen. Either a cocktail of different particulate antigens may be used, or a homogeneous population of particulate antigens having more than one epitope could be used (prepared, for example, by allowing a mixture of different hybrid proteins to aggregate into particles or by expressing more than one particulate antigen in the same cell); alternatively, a vaccine could contain a mixture of these sorts of particulate antigens.

In a further aspect, the invention provides nucleic acid comprising a first nucleotide sequence and second nucleotide sequence, wherein the first nucleotide sequence is substantially homologous with or complementary to genetic material in a retrotransposon or RNA retrovirus encoding a particle-forming protein, and wherein the second nucleotide sequence which encodes, an HIV antigen, to form a fusion protein which is not naturally produced by the said retrotransposon or RNA retrovirus.

It will generally be the case that the nucleic acid will be capable of being expressed without splicing or antitermination events. There will generally be no frameshifting.

In certain embodiments of the invention, we provide a TYA gene derivative that can be fused to an HIV antigen coding sequence to produce a TYA fusion gene. The TYA fusion gene produces a fusion protein that assembles into hybrid Ty-VLPs. These hybrid Ty-VLPs constitute a high molecular weight particulate antigen presentation system that can be produced in very high yields and that can be purified by simple physical procedures.

Further according to the present invention we provide an expression vector including nucleic acid as defined above. An example is pMA5620, which includes TYA gene derivative, and which directs the high level production of hybrid Ty-VLPs in yeast.

Expression vectors in accordance with the invention will usually contain a promoter. PGK is a preferred promoter, but any other promoter may be used if necessary or desirable. Examples includes GAPD, GAL1-10, PHO5, ADH1, CYC1, Ty delta sequence PYK and hybrid promoters made from components from more than one promoter (such as those listed).

The invention also includes host cells for example bacterial cells such as *E. coli,* yeast cells such as *S. cerevisiae,* or animal cells such as COS or CHO cells containing appropriate expression vectors.

Because of the polyvalent nature of the particulate antigens it is likely that it will be easier to produce antibodies than with conventional antigens and that those antibodies will have specific characteristics. The invention thus further provides antibodies raised against particulate antigens of the invention. The antibodies may be polyclonal (obtained for example by injecting antigens into a rabbit) or monoclonal antibodies, produced by hybridoma cells in accordance with the invention. Because of the polyvalent nature of the particulate antigens it is likely that in vitro immunisation can be achieved more readily than with other forms of antigen; this may facilitate the production of human monoclonal antibodies. Hybridoma cells may be prepare by fusing spleen cells from an immunised animal with a tumour cell. Appropriately secreting hybridoma cells may thereafter be selected. (See Koehler & Milstein Nature 1976 296 495).

The invention also provides a suitable technique for purifying HIV antigens. This aspect of the invention is based on the fact that it is generally relatively easy to separate particles from associate impurities (for example by filtration of centrifugation). Therefore, there is also provided a method of producing a substantially pure HIV antigen, the method comprising separating particles as described above from associated impurities and subsequently cleaving HIV antigen from the fusion proteins of the particles.

Fusion protein and particulate antigens of this invention are useful as diagnostic reagents. Particulate antigens are useful as diagnostic reagents. Particulate antigens for diagnostic purposes are particularly advantageous because they can be physically separated by centrifugation or filtration and can be directly dispersed on solid supports such as glass or plastic slides, dip sticks, macro or micro beads, test tubes, wells of microtiter plates and the like. The particulate antigens of this invention may also be dispersed in fibrous or bibulous materials such as absorbent disk (see U.S. Pat. No. 4,632,901), strips or chromatography columns as the solid support. The particles and fusion proteins readily adhere to solid supports. The particles may after purification be disrupted into fusion proteins and the fusion proteins may be dispersed on surfaces as indicated above. These reagents are useful for a variety of diagnostic tests. For example, a test sample suspected of having antibody to the particulate antigen and a fluorescent, enzyme or radio-labeled antibody is competitively reacted with the particulate antigen or fusion protein on a solid support and the amount of labeled antibody which binds to the particulate antigen on the solid support. Particulate antigens of this invention are also useful for agglutination reactions with antibodies. Those skilled in the diagnostic arts will recognize a wide variety of application of particulate antigens and fusion proteins of this invention for diagnostic purposes.

The invention is now illustrated by the following Examples, with reference to the accompanying drawings, in which the letter T followed by a number refers to MD40-4c transformed with a plasmid of that number:

FIG. 4 shows the nucleotide sequences around the BamHI sites of plasmids pMA5620, pMA5621 and pMA5622.

FIG. 6 shows the nucleotide sequence of the 5' ends of fragments hiv3 and hiv 10.

FIG. 10 is the nucleic acid sequence and deduced amino acid sequence of the p1:p24 fusion protein encoded by the plasmid pMA5620-hiv22.

FIG. 11 is the sequence of two synthetic HIV oligomers.

FIG. 12 is the nucleic acid sequence and deduced amino acid sequence of the p1:hiv31 fusion protein encoded by the plasmid pMA5620-hiv31.

FIG. 13 is the nucleic acid sequence and deduced amino acid sequence of the p1:hiv32 fusion protein encoded by the plasmid pMA5620-hiv32.

Figure 1:
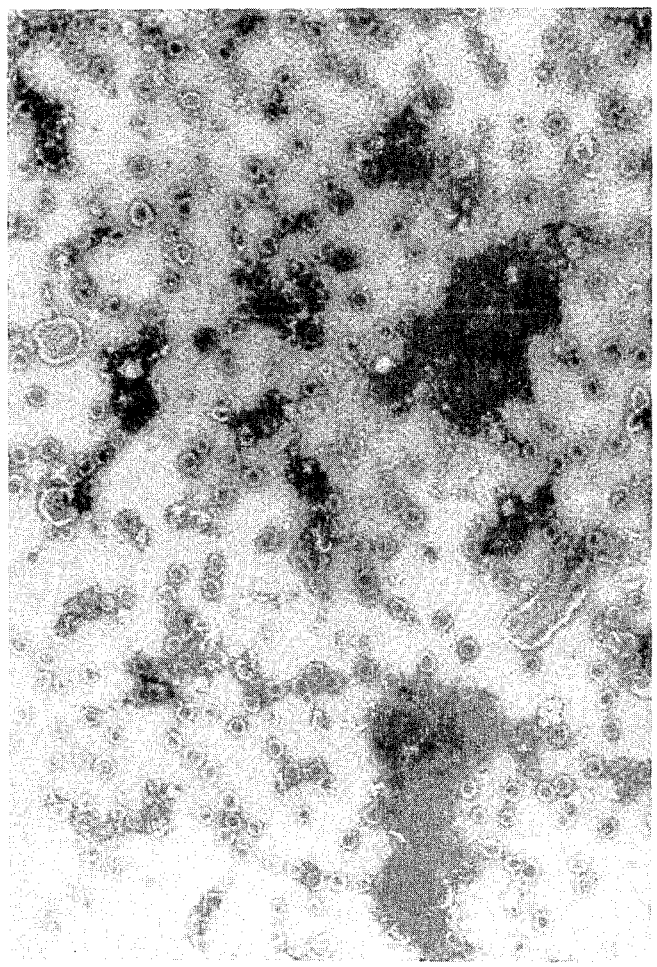
FIG. 1 is a photograph of Ty virus-like particles (Ty-VLPs) purified from MD40-4c transformed with plasmid pMA91-11.

The amino acid symbols in the drawings are as follows:

| The amino acid symbols in the drawings are as follows: | |
|---|---|
| Amino Acid | One-letter Symbol |
| Alanine | A |
| Arginine | R |
| Asparagine | N |
| Aspartic acid | D |
| Asn and/or Asp | B |
| Cysteine | C |
| Glutamine | Q |
| Glutamic acid | E |
| Gln and/or Glu | Z |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

EXAMPLE 1

Strains used were E. coli AKEC28 (C600, thyC, thvA, trpC1117, hsdRK, hsdK) and S. cerevisiae MD40-4c (urd2, tru1, leu2-3, leu2-112, his3-11, his3-15). E. coli media were prepared according to Miller (Miller 1972 Experiments in Molecular Genetics, CSH p433) and yeast media were prepared according to Hawthorne and Mortimer (Hawthorne and Mortimer 1960 Genetics 45, 1085).

E. coli was transformed using standard methods (Maniatis et al. 1982 Molecular cloning - A Laboratory Manual, CSH p199). Yeast was transformed as described by Hinnen et al. (Hinnen et al. 1978 Proc. Natl. Acad. Sci. 75, 1929).

Standard procedures were used for restriction digestion and plasmid constructions (Maniatis et al. 1982 op. cit). Restriction enzymes and T4 DNA ligase were used according to the suppliers instructions. Bal 31 exonuclease digestions were carried out as described by Dobson et al. (Dobson et al. 1982 Nucl. Acids Res. 10, 5463).

Deletion end points were determined by DNA sequencing (Sanger et al. 1977 Proc. Natl. Acad. Sci. 74, 5463). BamHI synthetic oligonucleotide linkers were obtained from Pharmacia.

Plasmid DNA was isolated from *E. coli* preparatively as described by Chinault and Carbon (Chinault and Carbon 1979 Gene 5, 111) and for rapid analysis by the method of Holmes and Quigley (Holmes and Quigley 1981 Anal. Biochem. 114, 193).

Ty-VLPs were purified as follows. Yeast cells were grown selectively at 30° C. to a density of $8 \times 10^6$ cells.ml$^{-1}$. The cells were then collected by low speed centrifugation, washed once in ice-cold water and resuspended in TEN buffer (10 mM Tris, pH 7.4; 2 mM EDTA; 140 mM NaCl) at 1 ml per 1 liter of cells. The cells were disrupted by vortexing with glass beads (40-mesh; BDH) at 4° C. until >70% were broken. The beads were pelleted by low speed centrifugation, then the supernatant was collected and the debris removed by centrifugation in a microfuge for 20 minutes. The Ty-VLPs were then pelleted from the supernatant by centrifugation at 100,000 g for 1 hour at 4° C. and by resuspended overnight in TEN buffer. The resuspended Ty-VLPs were centrifuged in a microfuge for 15 minutes at 4° C. to remove cell debris prior to loading the supernatant onto a 15–45% (w/v) sucrose gradient in 10 mM Tris, pH 7.4; 10 nM NaCl and spinning at 76,330 g for 3 hours at 15° C. Fractions were collected through the bottom of the tube and the peak fractions were identified by running aliquots of the fractions on SDS-PAGE gels and Coomassie blue straining. VLPs were concentrated by centrifugation of the peak fractions at 100,000 g for 1 hour at 4° C.

Protein extracts of whole yeast cells were prepared as previously described (Mellor et al. 1983 Gene 24, 1). Gel procedures were those of Laemmli (Laemmli 1970 Nature 227, 68). Protein concentrations were measured by a dye-binding assay (Bradford 1976 Anal. Biochem. 72, 248) obtained from Bio-Rad Laboratories.

Plasmic pMA91-11 has been described previously (Dobson et al. 1984 EMBO J. 3, 1115): it contains the first 1450 nucleotides of the major transcriptional unit of the Ty element, Ty1-15, inserted into the high efficiency expression vector pMA91 (Mellor et al. 1983 op. cit; Kingsman and Kingsman 1985 Biotech. and Genet. Eng. Rev. 3, 377). The Ty component was derived from pKT40b as described by Dolson et al. (op. cit); pKT40b has been deposited with the National Collection of Industrial Bacteria, Aberdeen, U.K. under accession number NCIB 12427. In turn, the expression vector pMA91 consists of plasmic pBR22 sequences which allow replication and selection in *E. coli*, the yeast 2 micron plasmid origin of replication, which allows efficient autonomous replication in yeast, the yeast LEU2 gene as a selectable marker in both yeast leu2 and *E. coli* leuB mutants and a Bg/II expression site which separates the upstream non-coding region of the yeast PGK gene from $-1500$ to $-1$ from the 3' region of PGK which contains all the signals for yeast transcription termination. Plasmid pMA91 is also described in U.S. Pat. No. 4,615,974, although it should be carefully noted that the plasmid designated as pMA3013 in FIG. 15 of this U.S. Patent is what is now known as plasmid pMA91. The plasmid shown in the lower part of FIG. 1 of U.S. Pat. No. 4,615,974 has since been renamed.

Ty expression is driven, therefore, from the promoter of the highly efficient yeast phosphoglycerate kinase gene (PGK) and yeast extracts of strains containing pMA91-11 overproduce massive amounts of p1 protein, the primary translation product of the TYA gene (Dobson et al. 1984 op. cit; Mellor et al. 1985a op. cit). We now demonstrate that extracts of yeast transformants containing pMA91-11 contain Ty-VLPs in large quantities (FIG. 1). Therefore, TYA alone contains sufficient information to make TyOVLPs and the p1 protein found in extracts of MD40-4c containing pMA91-11 is assembled into particles (FIG. 1).

Figure 2:
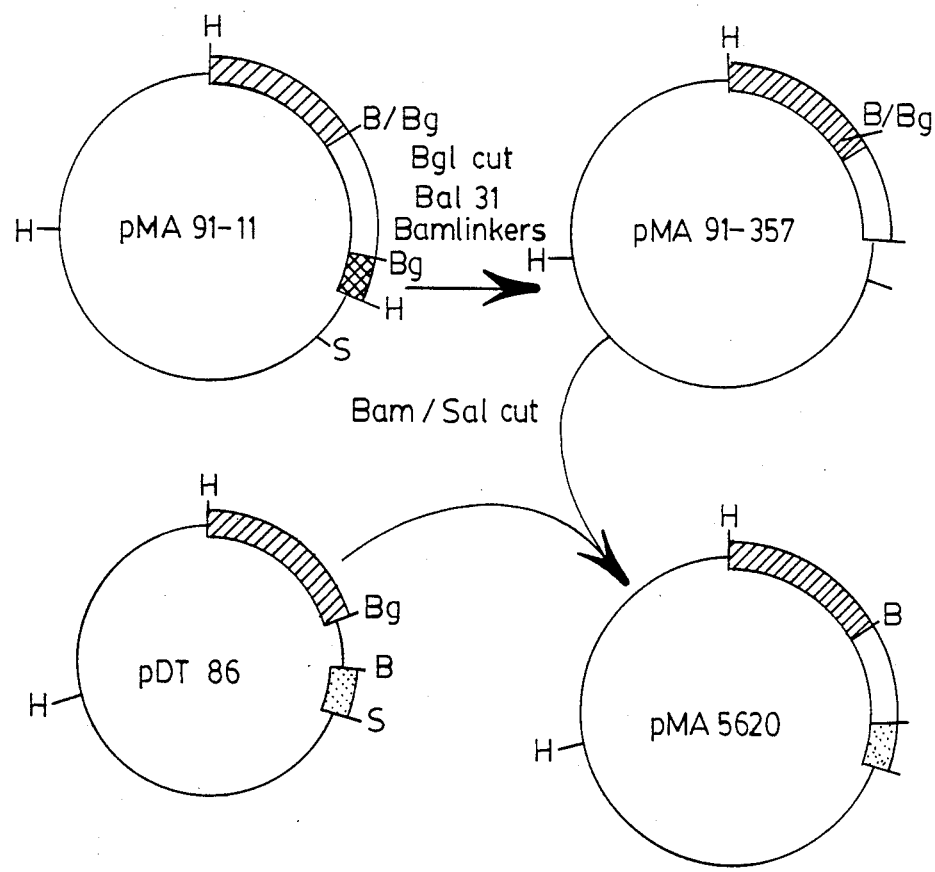
FIG. 2 is a schematic diagram of the construction of pMA5620.

The construction of a plasmid vector, pMA5620, that would direct the synthesis of any hybrid Ty-VLP particle is shown schematically in FIG. 2. This required the construction of a vector containing a convenient restriction endonuclease site within the TYA gene such that any coding sequence can be inserted into that site to create a TYA hybrid gene. However, it is essential that within such a hybrid there is sufficient TYA coding sequence to direct the synthesis of Ty-VLPs.

Plasmid pMA91-11 was cleaved with BglII, digested with Bal 31 exonuclease for various times and re-ligated in the presence of excess Bam HI linkers (CCGGATCCGG). The deletion end points of the resulting plasmids were determined by DNA sequencing. Plasmid pMA91-357 is a deletion derivative in which 265bp have been removed. This places the BamHI linker one nucleotide beyond codon 381 of TYA (FIG. 3).

In order to provide both transcription termination sequences and translation stop codons in all three reading frames the deleted PGK 3' terminator sequences of pMA91-357 were replaced with a 287 bp BamHI-SalI DNA fragment isolated from plasmid pDT86. This DNA fragment is a modified 3' transcription terminator fragment from the yeast PGK gene which contains translation stop codons in all three reading frames downstream of the BamHI site (FIG. 2). This terminator fragment starts with a BamHI linker (CCGGATCCGG) linked to the last sense codon of the PGK coding sequence and extends to the HindIII site 279 nucleotides beyond the PGK coding sequence (Hitzeman et al. 1982 Nucl. Acids Res. 10, 7791). In these constructions the HindIII site has been converted to a SalI site using synthetic linker. The terminator fragment is not critical and any fragment containing termination codons in all three reading frames followed by a yeast transcription terminator would suffice. The resulting plasmid, pMA5620, contains a unique BamHI site into which any suitable sequence can be inserted to produce a hybrid protein which will be assembled into hybrid Ty-VLPs.

Figure 3:
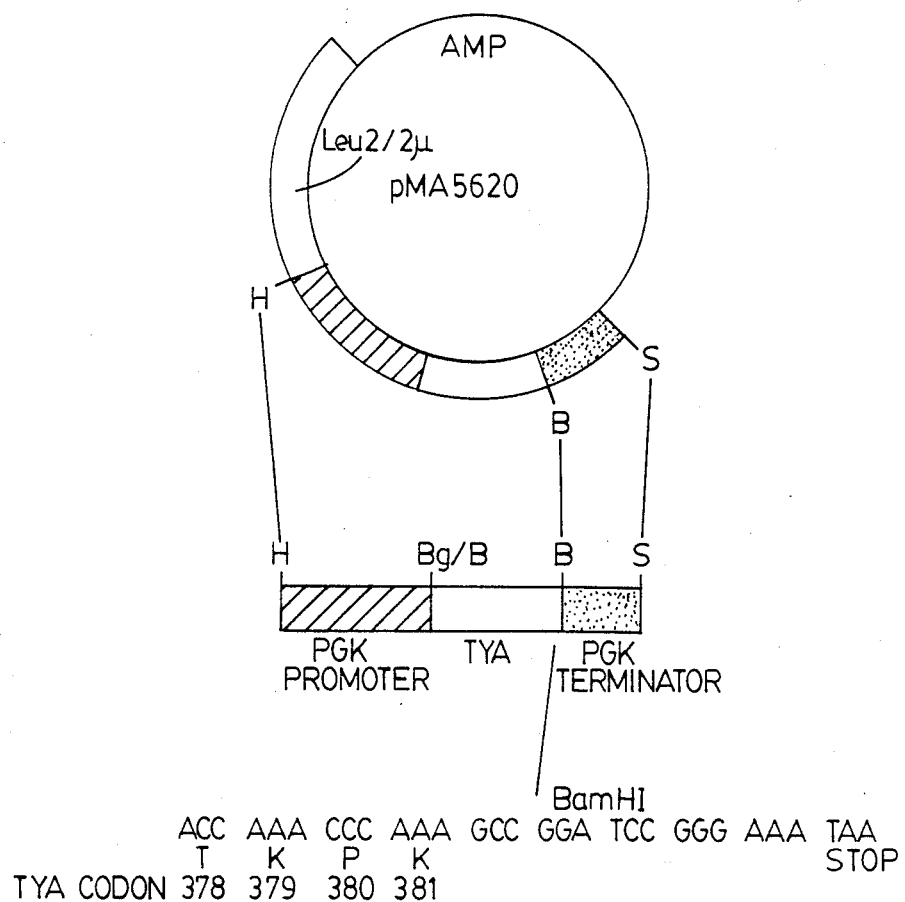
FIG. 3 is a diagram of plasmid pMA5620 with an expanded diagram of the key components of this example of the invention and the nucleotide sequence around the unique BamHI site.

Plasmid pMA5620 is shown in FIGS. 2 and 3. It can accept the coding sequence of any antigen at its unique BamHI site and then direct the synthesis in yeast of the resulting fusion protein. Clearly the antigen coding sequence must be inserted in such a way that it is in the same translational reading phase as TYA. In order to simplify this for any restriction fragment containing an antigen coding sequence two derivatives, pMA5621 and pMA5622, of pMA5620 were constructed in which cleavage points of their unique BamHI sites placed at positions that correspond to TYA translational reading phases +1 and +2. pMA5621 and pMA5622 were constructed by cleaving pMA5620 with BamHI, filling in the 5' extensions with DNA polymerase I and then ligating in the presence of oligonucleotide AAG-GATCC, for pMA5621, and oligonucleotide GGATCC for pMA5622. The sequence of the constructions was confirmed by dideoxynucleotide sequencing. FIG. 4 shows a comparison of the sequences of pMA5620, pMA5621 and pMA5622 around their unique BamHI sites with respect to the reading phase of TYA.

In order to produce hybrid Ty:HIV-VLPs it was necessary to insert fragments of the HIV proviral genome into pMA5620, pMA5621 and pMA5622. HIV DNA was from the proviral form of viral isolate HIV Ib (HTLV IIIb) as reported by Ratner et al. (1985 Nature 313, 277). Plasmid pHIVX is plasmid pSP46 (Promega Biotec) containing a 8931 bp SstI fragment that starts at the second SstI site of the provirus and ends at the third. This fragment contains therefore all of the viral coding regions and was the source of the HIV fragments.

Eight HIV fragments from the env coding region of the virus were chosen for an initial study. These were designated fragments hiv3, hiv4, hiv5, hiv6, hiv7, hiv8, hiv9 and hiv10. Fragment hiv3 is a KpnI:PvuII fragment corresponding approximately to codons 41 to 287; hiv4 is a DraI:HindIII fragment corresponding approximately to codons 341 to 639; hiv5 is a DraI:DraI fragment corresponding approximately to codons 129 to 341; hiv6 is a Sau3a:Sau3a fragment corresponding approximately to codons 25 to 112; hiv7 is a Sau3a:Sau3a fragment corresponding approximately to codons 112 to 272; hiv8 is a Sau3a:Sau3a fragment corresponding approximately to codons 272 to 466; hiv9 is a Sau3a:Sau3a fragment corresponding approximately to codons 466 to 588; hiv10 is a Sau3a:Sau3a fragment corresponding approximately to codons 588 to 743.

Figure 5:
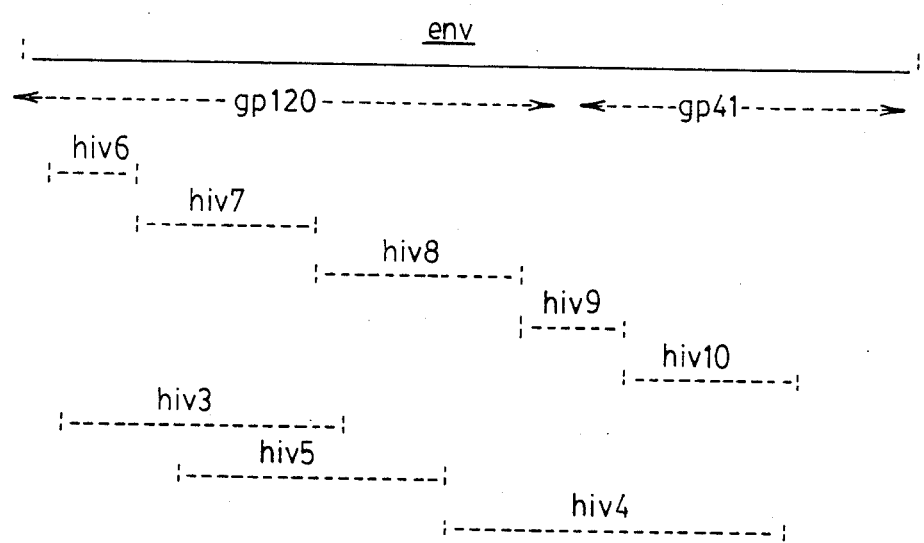
FIG. 5 shows the approximate position of fragments hiv3 to hiv 10 on the map of the env region of HIV.

FIG. 5 shows the approximate positions of these fragments on a map of the HIV env region. Each of the fragments were purified from agarose gels and inserted into either pMA5620, pMA5621 or pMA5622 by various means: hiv8 was inserted via a sticky-end ligation into pMA5620 to produce pMA5620-hiv8; hiv6 and hiv9 were inserted into pMA5621 via sticky-end ligations to produce pMA5621-hiv6 and pMA5621-hiv9 respectively; hiv7 and hiv10 were inserted into pMA5622 via sticky-end ligations; hiv4 and hiv5 sticky-ends were filled in by DNA polymerase I and then the fragments were blunt-end ligated into pMA5620 that had been cleaved at the BamHI site and also filled in to produce pMA5620-hiv4 and pMA5620-hiv5; hiv3 stickey-ends were filled in and then the fragment was blunt-end ligated into pMA5621 that had been cleaved at the BamHI site and also filled in to produce pMA5621-hiv3. FIG. 6 shows the nucleotide sequence of the 5' ends of the hiv3-10 fragments.

Figure 7:
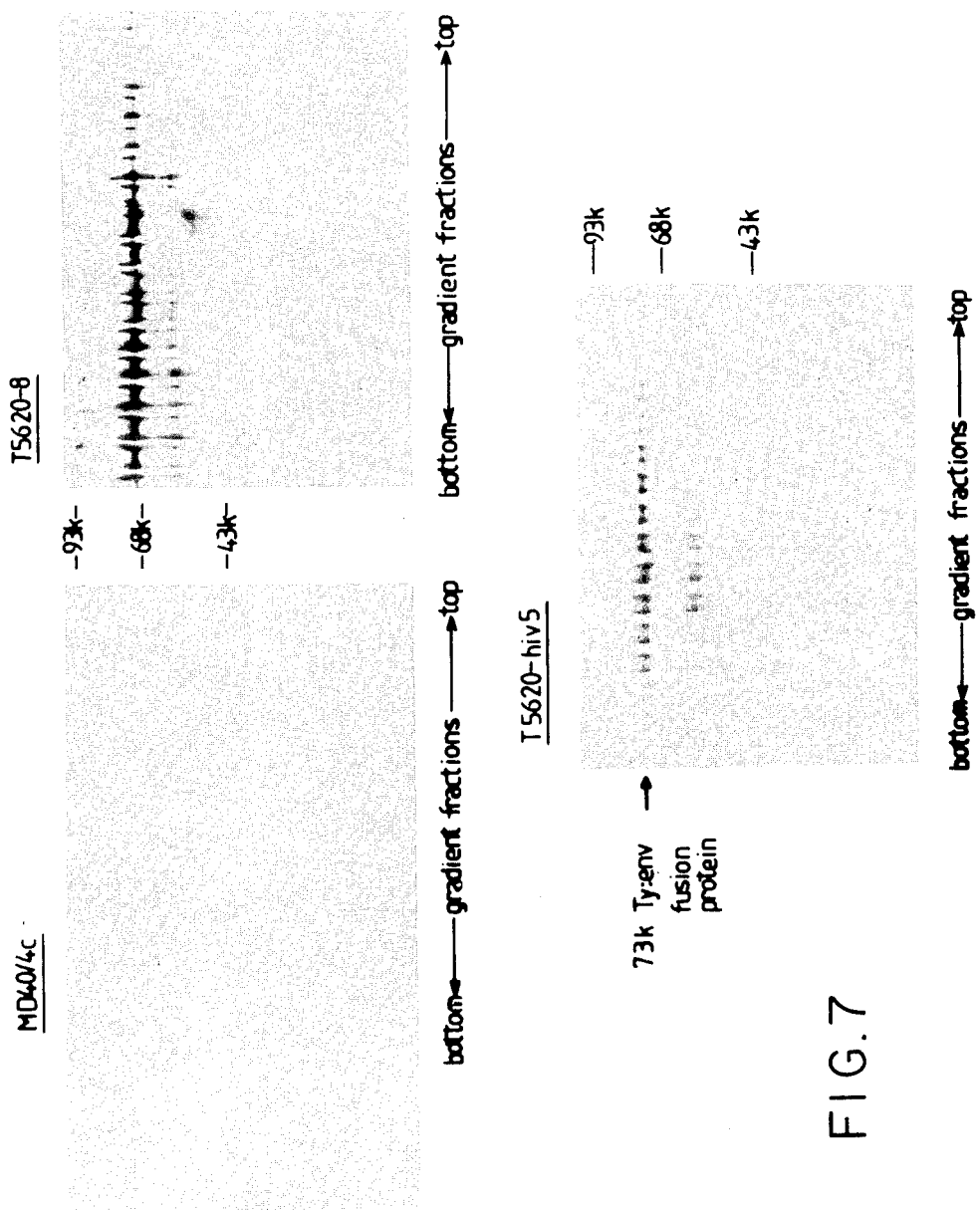
FIG. 7 shows a Western blot of sucrose gradient fractions from extracts of MD40-4c and MD40-4c transformed with pMA5620-hiv5 and pMA5620-8. The blotted proteins are probed with anti-Ty-VLP antibody.

Each of the plasmids was used to transform yeast strain MD40-4c to leucine independence. Extracts of the resulting transformants were then analysed for the presence of hybrid Ty:HIV-VLPs. VLPs were prepared from transformants and fractions from a 15–45% sucrose gradient were run on an SDS-PAGE gel. The proteins were visualised by Western blotting and then probing with an anti-Ty-VLP antibody. FIG. 7 shows the results for PMA5620-hiv5.

Figure 8:
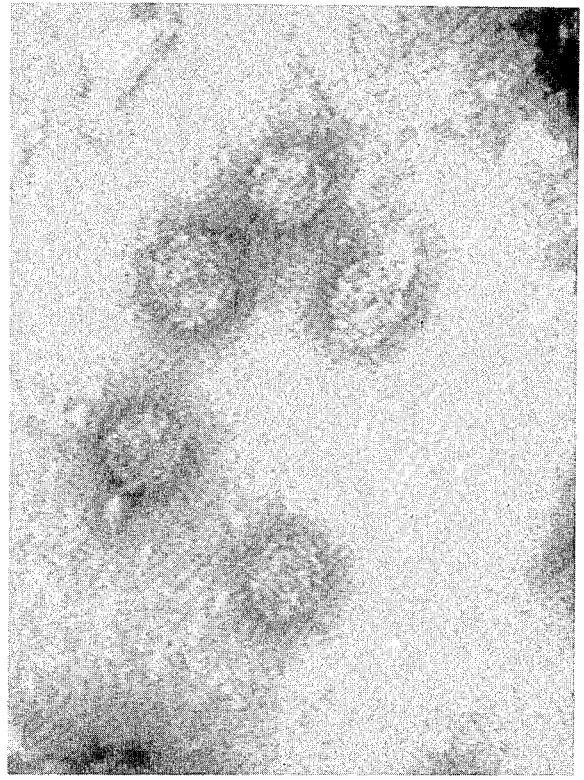
FIG. 8 shows an electron micrograph of hybrid Ty:-HIV-VLPs produced from pMA5620-hiv5.

The fusion of the part of TYA present in pMA5620 to hiv5 should produce a new Ty:HIV protein of about 70 kd. This protein, if it is in particulate form, should co-migrate with the particles in extracts of MD404c transformed with pMA5620-hiv5 but contains an interferon-alpha2 cDNA instead of an hiv5 fragment (UK patent application No. 8626148). The data in FIG. 7 show that this is the case suggesting that pMA5620-hiv5 directs the production of hybrid Ty:HIV-VLPs. Similar results are obtained with the other constructions. The fractions of the sucrose gradient that contained the 70 kd fusion protein were examined by electron microscopy and were shown to contain particles (FIG. 8). We would conclude therefore that pMA5620-hiv5 directs the production of hybrid Ty:HIV-VLPs.

In order to establish that these VLPs do in fact carry HIV epitopes fractions containing particles from the sucrose gradients may be pooled and samples were run on an SDS-PAGE, electroblotted onto nitrocellulose and then probed with anti-HIV antiserum. As a positive control for this experiment disrupted HIV may be run alongside the particle proteins.

EXAMPLE 2

In order to test the efficacy of the hybrid Ty:HIV-VLPs produced as in Example 1 in eliciting an immune response to the HIV component antisera are raised in rabbits against concentrated hybrid Ty:HIV-VLPs purified from MD40-4c transformed with pMA5620-hiv5 and pMA5620-hiv8. These antisera are then used in a Western blot against disrupted HIV, from which it may be seen that they react showing that the hybrid Ty:-HIV-VLPs induce the production of anti-HIV antibodies.

It is important that an antigen that is to be used as a vaccine induces the production of neutralising antibodies. To test this for the hybrid Ty:HIV-VLPs the antisera are tested in an HIV infectivity neutralisation assay, from which it may be seen that the antisera will neutralise HIV showing that the hybrid Ty:HIV-VLPs are useful as a vaccine.

. These data show: (1) fusion proteins composed of 381 amino acids of the TYA gene and various fragments from HIV are readily produced: (2) these fusion proteins produce polyvalent hybrid Ty:HIV-VLPs; (3) these hybrid Ty:HIV-VLPs react with anti-HIV antiserum; (4) the hybrid Ty:HIV-VLPs induce the production of neutralising anti-HIV antibodies in rabbits. It is reasonable therefore to expect that pMA5620, pMA5621 or pMA5622 will direct the expression of polyvalent hybrid Ty:HIV-VLPs containing any HIV antigen from gag, pol, env, sor, tat, art/trs or 3'ort. Any of these antigens may constitute a key component in a vaccine or a diagnostic kit.

EXAMPLE 3

The Production of Hybrid HIV:TY-VLPS Carrying p24 Antigens

The HIV gag precursor protein is cleaved into three mature proteins p17, p24 and p15, that form the virus core. The p24 protein is particularly significant from a diagnostics point of view as HIV positive assymptomatic individuals have high titres of anti-p24 antibody. Furthermore, p24 may be significant in the production of a vaccine (Salk, 1987, Nature 327. 473).

Figure 9:
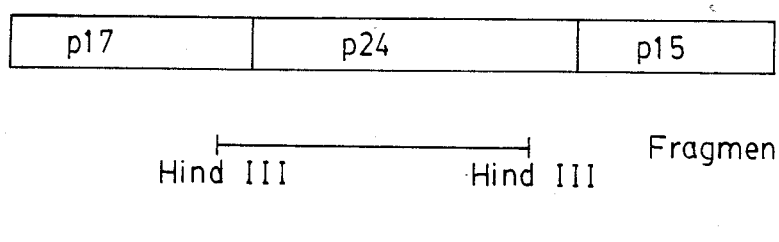
FIG. 9 is a diagram of the approximate position of fragment hiv22 on the map of the gag region of HIV and the nucleotide sequence and amino acid sequence at the TYA-hiv22 junction in the plasmid pMA5620-hiv22.

In order to construct hybrid HIV:Ty-VLPs carrying p24 antigens, a HindIII fragment, hiv22, from the gag gene of the HIV proviral genome was inserted in the BamHI site of pMA5620. hiv22 starts at nucleotide 1082 and ends at 1709 (Ratner et al; 1985 Nature 313, 277) and it encodes amino acids 99 to 308 of gag. This region contains, therefore, the carboxy-end of p17 and most of p24 (FIG. 9). hiv22 was inserted into pMA5620 such that the TYA and gag sequences were in frame (FIG. 9) and the resulting molecule was designated pMA5620-hiv22. This plasmid was introduced into yeast strain MD40-4c and extracts of the transformants were analysed on 15–45% sucrose gradients. Coomassie stained SDS-PAGE gels of the gradient fractions revealed the presence of a fusion protein of about 75 kd, the expected size of a p1:p24 fusion protein, in the region of the gradient characteristic of particulate structures. That this protein carries p24 antigens was confirmed by blotting a similar gel and probing with a p24 monoclonal antibody. This showed a clear peak of reacting material well down the gradient at a position diagnostic of particulate structures. The particulate nature of the p1:p24 fusion was further confirmed by examining peak fractions in the electron microscope. Numerous particles were seen. FIG. 10 shows the amino acid sequence and nucleotide coding for p1-p24.

These data show that hybrid HIV:Ty-VLPs carrying p24 antigens can be produced and that the antigen reacts with an anti-p24 monoclonal antibody. This system may be used to produce p24 antigens for diagnostics or an anti-HIV vaccine.

EXAMPLE 4

Synthetic Oligonucleotides to Produce Ty:HIV Fusion Genes

The oligonucleotides were synthesized by automated phosphoramidite chemistry using cyanoethyl phosphoramidites (Beaucage and Caruthers 1981 Tetrahedron Letters 24, 245). Following de-blocking and removal from the controlled pore glass support the oligomers were purified on denaturing polyacrylamide gels, further purified by ethanol precipitation and finally dissolved in water prior to estimation of their concentration. The oligomers were then kinased to provide them with a 5' phosphate as required for the ligation step. Complementary oligomers were then annealed prior to ligation into the relevant plasmid vector. The sequence of the synthetic oligomers was confirmed by dideoxy sequencing. The protocol used was essentially as has been described (Biggin et al. 1983 Proc. Natl. Acad. Sci, 80 m 3963) and modified to allow sequencing on plasmid DNA as described (Guo and Wu 1983 Nucl. Acids Res. 11, 5521).

In order to construct hybrid HIV:Ty-VLPs carrying env antigens two DNA oligomers were synthesized. Oligomer hiv31 is 105 bp in length and encodes amino acids 495 to 527 of the env precursor protein gp160 of HIV 1b (HTLVIIIb; Ratner et al. 1985 Nature 313 277): it spans the cleavage site between gp120 and gp41. Oligomer hiv32 is 114 bp in length and encodes amino acids 53 to 88 of gp120 of HIV1b (HTLVIIIb; Ratner et al; 1985 Nature 313, 277). The codons were selected to be those that are favored by yeast (Maruyama et al. Nucl. Acids Res. Suppl. 14, 151). The end points of the oligomers were designed such that following ligation into pMA5620 cleaved with BamHI. a BamHI site would be re-created at the 3, end of the insertion and a BamHI/BglII junction generated at the 5' end (FIG. 10).

The synthetic oligomers hiv31 and hiv32 (FIG. 11) were ligated into pMA5620 that had been cleaved at the BamHI site. The resulting plasmids are designated pMA5620-hiv31 and pMA5620-hiv32. The complete nucleotide sequence and the deduced amino acid sequence of the HIV:Ty fusion proteins encoded by these two plasmids is shown in FIGS. 12 and 13.

Plasmids pMA5620-hiv31 and pMA5620-hiv32 were used to transform yeast strain MD40-4c to leucine independence. Extracts of the resulting transformants were then analysed for the presence of hybrid HIV:Ty-VLPs. VLPs were prepared from the transformants and franctions from a 15–45% sucrose gradient were run on SDS-PAGE gels. In both cases Coomassie blue standing revealed the presence of a fusion protein of about 54 kD, the expected size of both of the HIV:Ty fusion proteins, in the region of the gradient characteristic of particulate structures, although it is noticable that the precise position differs for the two types of particles.

These data show that synthesized oligomers can be used in the construction of hybrid HIV:Ty fusion genes. Overexpression of these genes results in the production of hybrid HIV:Ty-VLPs. This system could be used to produce defined env antigens for diagnostics or an anti-HIV vaccine.

EXAMPLE 5

Enzyme Immunoassay Procedure with VLP Having an HIV Antigen 96-well microtitre plates are coated with VLP having a fused HIV antigen (VLP-HIV) by incubating 50 μl of 20 μg/ml of VLPs in 50 mM sodium carbonate buffer, pH 9.5, in each well for two hours at room temperature. Excess VLPs HIV are washed out of the wells by three, five minute washes with phosphate buffered saline (PBS), pH 7.4. In order to minimize background reactions, the wells are blocked with 100 μl of 2% casein in PBS for one hour at room temperature, followed by three, five minute washes with PBS containing 0.1% Tween-20 (PBS-T). A test sample is suitably diluted in PBS-T containing 0.5% casein (PBS-CT). A suitable dilution may be a three-fold dilution series from 1/10 to 1/7,290. The HIV antibody in the test sample is reactive to the HIV component of any hybrid VLP-HIV. 50 μl of diluted test sample antibody is added to the appropriate wells and incubated for two hours at room temperature. Excess test sample antibody is removed by three, five minute washes with PBS-T. Secondary antibody is horseradish peroxidase-labeled anti-species IgG, and is diluted 1/1,500 in PBS-CT. 50 μl of diluted secondary antibody is added to each well and incubated for two hours at room temperature, followed by five, five minute washes with PBS-T. The substrate is 3,3',5,5'-tetramethylbenzidine at a concentration of 0.1 mg/ml in 0.1 M sodium acetate, adjusted to pH 6.0 with 0.5 M citric acid, plus 0.03% hydrogen peroxide. 50 μl of substrate is added to each well and the color reaction developed for 10 minutes. The reaction is terminated by the addition of 25 μl of 0.5 M sulfuric acid to each well. Color development is assessed by measurement at 450 nm using a microplate reader. In this way a direct assay of the HIV antibody in the test sample is performed.

What is claimed is:

1. A particle comprising a plurality of fusion proteins, each fusion protein comprising a first amino acid sequence and a second amino acid sequence, wherein the first amino acid sequence is substantially homologous with a particle-forming protein encoded by a yeast TYA gene without TYB gene sequence and wherein the second amino acid sequence is substantially homologous to an HIV antigen.

2. A diagnostic reagent comprising particles of claim 1 dispersed on a solid support.

3. A particle according to claim 1 wherein the second amino acid sequence is immunologically reactive to antibodies which are immunologically reactive to HIV proteins p24, p41 or p120.

* * * * *

UNITED STATES PATENT AND TRADEMARK OFFICE
CERTIFICATE OF CORRECTION

PATENT NO. : 4,918,166

DATED : April 17, 1990

INVENTOR(S) : Alan J. Kingsman, et al

Page 1 of 2

It is certified that error appears in the above-identified patent and that said Letters Patent is hereby corrected as shown below:

In the Abstract:
line 1, "a77" should read merely --a--.

Column 1, line 25, "324 691" should read --324, 691--; line 28, "know" should read --known--; line 30, "313 450" should read --313, 450--; line 31, "227 484" should read --227, 484--; line 34, "tat." should read --tat,--; line 45, "(1986) Science 234 1392" should read --1986 Science 234, 1392--; line 46, "233 209" should read --233, 209--; line 51, "231 1556" should read --231, 1556--; line 52, "5 3065" should read --5, 3065--; line 57, "5 3051" should read --5, 3051--; line 59, "83 6672" should read --83, 6672--; line 59, "231 1553" should read --231, 1553--; line 60, "233 1289" should read --233, 1289--; line 61, "231 1580" should read --231, 1580--.

Column 3, lines 12-13, "Virus. SIV," should read --Virus, SIV,--; line 17, "melanozasterm" should read --melanogaster--; line 43, "(NAR 14(17) 1986 7001)." should read --(1986 NAR 14(17), 7001).--; line 67, "purifications" should read --purification--.

Column 4, lines 46-47, "includes TYA gene" should read --includes a TYA gene--.

Column 5, line 2, "in vitro" should be either in italics or underlined; line 2, "immunisation" should read --immunization--; line 5, "prepare" should read --prepared--; lines 8-9, "(See Koehler & Milstein *Nature* 1976 296 495)." should read --(See Kohler & Milstein 1976 Nature 296, 495).--; line 14, "of" should read --or--.

Column 6, line 59, "cloning" should read --Cloning--.

Column 7, line 11, "30° C." should read --30° C--; line 12, "cells.ml$^{-1}$" should read --cells/ml$^{-1}$--; line 17, "4° C." should read --4° C--; line 22, "4° C." should read --4° C--; line 22, "and by" should read --and were--; line 25, "4° C." should read --4° C--; line 40, "Plasmic" should read --Plasmid--; line 47, "Dolson" should read --Dobson--; line 51, "pBR22" should read --pBR322--; line 56, "Bg/II" should read --BglII--.

UNITED STATES PATENT AND TRADEMARK OFFICE
CERTIFICATE OF CORRECTION

PATENT NO. : 4,918,166

Page 2 of 2

DATED : April 17, 1990

INVENTOR(S) : Alan J. Kingsman, et al

It is certified that error appears in the above-identified patent and that said Letters Patent is hereby corrected as shown below:

Column 8, line 7, "TyOVLPs" should read --Ty-VLPs--; line 21, "Bam HI" should read --BamHI--.

Column 9, lines 8-9, "HIV Ib" should read --HIV IIIb--; line 59, "PMA5620-hiv5" should read --pMA5620-hiv5--; line 63, "MD404c" should read --MD40-4c--.

Column 10, line 43, "3'ort" should read --3'orf--; line 49, "HIV:TY-VLPS" should read --HIV:Ty-VLPs--; lines 54-55, "assymptomatic" should be spelled --asymptomatic--; line 57, "Salk, 1987, Nature 327 473" should read --Salk 1987 Nature 327, 473--.

Column 11, line 40, "Proc. Natl. Acad. Sci, 80m 3963" should read --Proc. Natl. Acad. Sci. 80m, 3963--; line 50, HIVIb (HTLVIIIb" should read --HIV IIIb (HTLV IIIb--; line 51, "al;" should be --al.--; line 55, "cleaved with BamHI. a BamHI site" should read --cleaved with BamHI, a BamHI site--.

In the Claims:
Claim 3, line 67, the phrase "proteins p24, p41 or p120" should read --proteins p24, gp41 or gp120--.

Signed and Sealed this

Twenty-second Day of September, 1992

Attest:

DOUGLAS B. COMER

*Attesting Officer*     *Acting Commissioner of Patents and Trademarks*